United States Patent [19]

Williams et al.

[11] Plant 4,321

[45] Oct. 24, 1978

[54] APPLE TREE (COOP 10)

[75] Inventors: Edwin B. Williams, Lafayette; Jules Janick; Frank H. Emerson, both of West Lafayette, all of Ind.; Daniel F. Dayton, Urbana, Ill.; L. Fredrick Hough, Bloomsbury; Catherine Bailey, Englishtown, both of N.J.

[73] Assignee: Purdue Research Foundation, West Lafayette, Ind.

[21] Appl. No.: 821,642

[22] Filed: Aug. 4, 1977

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

This invention relates to an apple tree cultivar, said apple tree being scab resistant and having a fruit maturity about 1 week after Delicious and 4½ weeks after Prima.

1 Drawing Figure

1

This invention is a new and distinct cultivar of apple tree. It was discovered by applicants in September, 1970, at Lafayette, Ind., in the course of an attempt to develop improved apple trees with high fruit quality and resistance to *Venturia inaequalis* (Cke.) Wint., the causal agent for the apple scab disease. The tree is a seedling of known parentage planted in 1962 in Block A of the Hinsley Breeding Orchard at the Horticulture Farm of the Purdue University Agricultural Experiment Station, Lafayette, Ind. In the above orchard, its position was Row 4, Tree 132, having the description PRI1659-10 in our breeding records.

The present new cultivar, which is designated as Coop 10, is a seedling produced from crossing 'Starking Delicious' as the seed parent and the seedling PRI610-2 as the pollen parent in 1961 in Door County, Wis. This new cultivar carries a genetic factor, $V_f$ inherited from *Malus floribunda* 821 which causes it to be resistant to infection caused by *Venturia inaequalis.* The presence of this genetic factor has been repeatedly proven by controlled greenhouse inoculation tests of the seedling and of its offspring produced from controlled crosses. The complete pedigree is shown below.

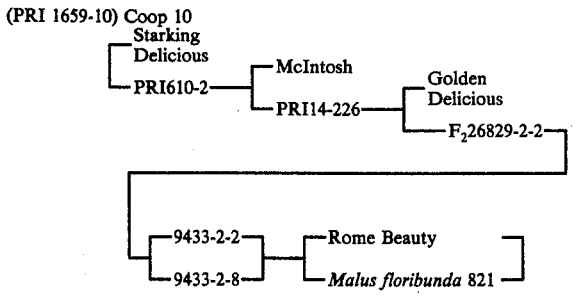

The new cultivar produces a moderately spreading and vigorous tree. The tree is productive and has a tendency to become biennial unless controlled by thinning. It is resistant to scab and cedar rust and shows moderate field resistance to fireblight and powdery mildew.

The tree flowers with 'McIntosh' and with 'Priscilla' which is described in U.S. Plant Pat. No. 3,488. The apple fruit has good dessert quality with pleasant flavor and aroma. The characteristic flavor is maintained three months or more at 34° F. Fruits do not dehydrate after

2 extended storage. The fruit has a tendency to drop at maturity.

After observation, the selection was asexually propagated by grafting on seedling apple roots. The grated material has maintained the described characteristics after propagation.

The accompanying drawing (color photograph) shows a typical example of fruit and foliage of Coop 10. The following is a detailed description of this new cultivar with the color designation according to the Horticultural Colour Chart issued by the British Colour Council in collaboration with the Royal Horticultural Society.

FLOWER

Pedicel: 3 cm (1¼ inches) in length.
Corolla: 4.5 cm (1⅝ inches) in diameter at anthesis.
Color: Fuchsia purple from plate 28/1 (bud) to 28/3 and paler (open flowers).

FRUIT

Shape: Conic, regular.
Size: Axial diameter 7.5 cm (3 inch). Transverse diameter 7.5 cm (3 inch).
Color: Empire yellow (plate 603/1, occasional scarlet blush (Plates 19/1 to 19/2) on exposure.
Skin: Smooth, waxy, inconspicuous dots, medium thick but not tough.
Stem: 2.5 cm (1 inch), medium thickness.
Cavity: Acute, deep, medium width, russeted.
Basin: Medium depth and breadth.
Calyx: Persistent, upright, partly closed.
Calyx tube: Urn-shaped.
Stamens: Medium.
Core line: Meeting.
Core: Medium, open, large.
Carpels: Mucronate, cordate, smooth.
Seed: Obtuse, not tufted.
Flesh:
*Texture.*—Medium to coarse grained, firm.
*Quality.*—Good, mild subacid, aromatic.
*Color.*—Primrose yellow (Plate 601/3).
Maturity season: One week after "Delicious".
Keeping quality: Retains quality three months or more at 34° F.
Use: Dessert apple.

TREE

Tree: Moderately spreading and vigorous.

Leaves: Ovate, single serrate margin, apex acute, base rounded, length to width ratio = 1.6.

In particular our new cultivar apple is distinguished by its resistance to scab and good dessert quality.

We claim:

1. A new and distinct apple tree substantially as shown and described, particularly characterized by resistance to apple scab, good fresh fruit quality, smooth waxy skin, aromatic, ability to maintain quality in storage without shriveling and maturing approximately 1 week after 'Delicious', along with 'Golden Delicious' and 4½ weeks after 'Prima'.

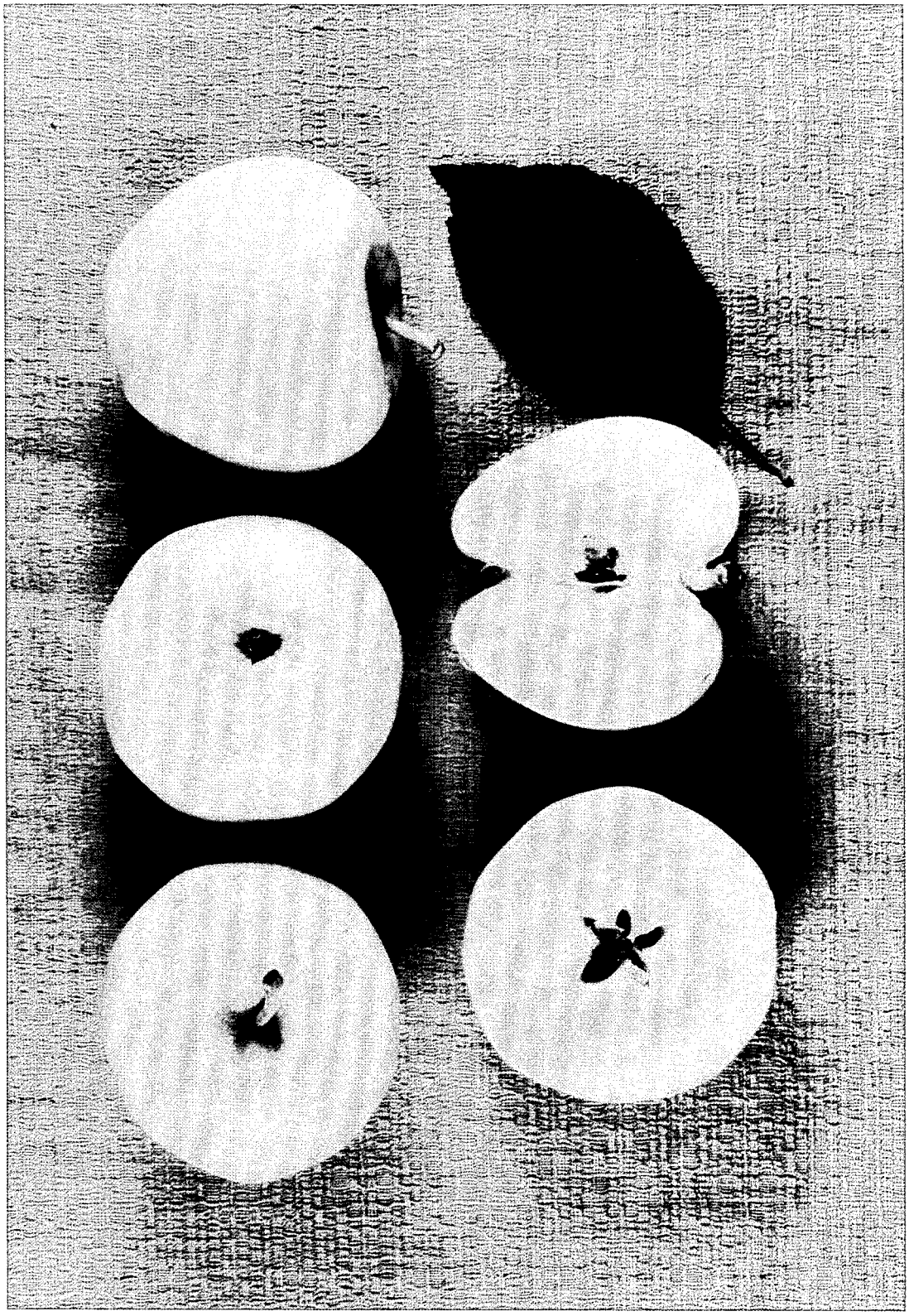

* * * * *